United States Patent [19]

Mouk et al.

[11] Patent Number: 5,698,750
[45] Date of Patent: Dec. 16, 1997

[54] METHODS FOR PURIFYING AND RECOVERING CONTAMINATED REFRIGERANTS WITH AQUEOUS SOLUTIONS OF BASES

[75] Inventors: Robert W. Mouk, Westerville; Albert E. Abel, Powell, both of Ohio

[73] Assignee: Commodore Laboratories, Inc., Columbus, Ohio

[21] Appl. No.: 550,458

[22] Filed: Oct. 30, 1995

Related U.S. Application Data

[63] Continuation-in-part of Ser. No. 207,286, Mar. 7, 1994, abandoned.
[51] Int. Cl.$^6$ .................................................. C07C 17/38
[52] U.S. Cl. .............................................. 570/177; 570/262
[58] Field of Search ........................................ 570/177, 262

[56] References Cited

U.S. PATENT DOCUMENTS

| | | | |
|---|---|---|---|
| 2,738,371 | 3/1956 | Parmalee | 570/177 |
| 2,999,885 | 9/1961 | Heberling | 570/177 |

FOREIGN PATENT DOCUMENTS

| | | | |
|---|---|---|---|
| 4205341 | 8/1993 | Germany | 570/177 |

OTHER PUBLICATIONS

Takao Hayashi, Kogyo Kagaku Zasshi, Oct. 1965, vol. 68, No. 10, 2002.

*Primary Examiner*—Alan Siegel
*Attorney, Agent, or Firm*—Howard M. Ellis; Marianne Fuierer; Richard L. Hansen

[57] ABSTRACT

Refrigerants, such as Freon® 12 and other potential ozone depleting substances will be in short supply as their production is phased out, and until existing refrigeration equipment is retrofitted to receive more environmentally friendly refrigerants. Existing supplies of such refrigerants when contaminated with other refrigerants especially hydrofluoroalkanes like Freon 22 can form azeotropes, which are not readily separated by conventional distillation methods, are selectively decomposed in-situ by reacting with aqueous solutions of metal hydroxides or other bases. The remaining non-reacted refrigerant-containing composition is readily recycled by separation and recovery methods from the reaction mixture to provide a reusable refrigerant composition virtually free of contaminating refrigerant.

45 Claims, No Drawings

METHODS FOR PURIFYING AND RECOVERING CONTAMINATED REFRIGERANTS WITH AQUEOUS SOLUTIONS OF BASES

CROSS REFERENCE TO RELATED APPLICATION

This application is a continuation-in-part of application Ser. No. 08/207,286, filed Mar. 7, 1994 now abandoned.

TECHNICAL FIELD

The present invention relates generally to the reclamation of chlorofluorocarbons (CFCs), and more specifically, to methods of purifying and recovering refrigerants from refrigerant mixtures for recycling or for reuse as refrigerants, especially in air conditioning and refrigeration equipment.

BACKGROUND OF THE INVENTION

Chlorofluorocarbons (CFCs) are synthetic chemical compounds widely used in refrigeration and air conditioning; as aerosol propellants and solvents; in forming foams, including those used in fast-food packaging; and in rigid insulation. Scientists now see these synthetic chemicals as the main threat to Earth's protective ozone layer. Because CFCs are immune to destruction in the troposphere, and because they eventually float upwardly, their manufacture and release have lead to the accumulation of large amounts in the stratosphere. In the stratosphere, CFCs are broken down by sunlight into chlorine, which has a catalytic and destructive effect on ozone. The result has been a significant decline in the global ozone shield and an increase in the amount of harmful ultraviolet radiation reaching the surface of Earth. According to a United Nations' study, every 1 percent drop in ozone will lead to a 3 percent increase in non-melanoma skin cancers in light-skinned people, as well as dramatic increases in cataracts, lethal melanoma cancers, and damage to the human immune system. Higher levels of UV light may also worsen ground-level pollution and hurt plants, animals, and especially light sensitive aquatic organisms.

As a result, destruction of CFCs, and in some instances, reclamation of CFC refrigerants is a vital component of the national and global strategies for protection of the earth's ozone layer in a manner consistent with minimal economic disruptions associated with the phase-out of this class of chemicals. There are still sizable reserves of CFCs on hand which must be treated and converted to environmentally benign substances. Likewise, until existing refrigeration and air conditioning equipment is replaced or retrofitted with devices which are capable of operating with more environmentally friendly refrigerants, as CFC production is curtailed and eventually eliminated, industry and consumers must rely increasingly on the availability of reclaimed refrigerants which have been purified.

However, reclamation, particularly of previously used refrigerants, is frequently hampered due to cross-contamination occurring with other refrigerants. In this connection, environmental regulatory laws and rules prohibit the discharge of refrigerants into the atmosphere from air conditioning and refrigeration equipment when servicing motor vehicles, commercial and residential installations. As a result, businesses providing such services have adopted the practice of collecting by bleeding or discharging "used" refrigerants from systems into collection tanks or refrigeration recovery systems during servicing. However, in the practice of collecting used refrigerants from air conditioning and refrigeration systems the present inventors observed that cross-contamination occurs when one or more chemically dissimilar refrigerants are inadvertently or carelessly discharged into common collection vessels/cylinders intended for storing but a single type/grade of refrigerant. Consequently, significant quantities of potentially reusable refrigerants cannot be readily recycled because of contamination with excessive amounts of unwanted other refrigerants.

In order to qualify for reuse, used refrigerants are required to meet the American Refrigeration Institute's "700" specifications for purity which stipulate the permissible levels of contaminants. That is, strict limits are placed on moisture, particulates, acidity, oil content, non-condensible gases, and other refrigerants present. Existing reclamation processes are capable of meeting all of the foregoing criteria with the exception of "other refrigerants", which are not permitted to exceed 0.5 percent.

One example of a widely used refrigerant is Freon® 12, a trademark of E. I. DuPont, which is dichlorodifluoromethane. The present inventors discovered in reclaiming previously used Freon 12, hereinafter called R-12, that it can also be contaminated with seemingly minor amounts of Freon 22, which is chlorodifluoromethane, hereinafter called R-22. Although removal of the unwanted R-22 contaminant from such a mixture would appear to be readily accomplished by distillation due to differences in their boiling points (R-12 b.p. −29.8° C. and R-22 b.p. −41° C.), separation by distillation is not always readily achieved because of the formation of an azeotrope when the two refrigerants become mixed.

Quite significantly, the present inventors discovered that an aqueous solution of a base, such as sodium hydroxide can be efficiently employed in a highly economic process of purifying contaminated refrigerant mixtures, and particularly previously used refrigerants which have become cross-contaminated with unacceptably high levels of "other refrigerants" during collection, handling or storage. Accordingly, the methods are especially useful in reclamation processes where the manufacture of certain CFCs, such as R-12 are being phased-out of production, but market demand remains strong.

The hydrolysis Of chlorodifluoromethane (R-22) in aqueous sodium hydroxide was disclosed by Takao Hayashi in a paper entitled "Preparation of Sodium Formate by Hydrolysis of Chlorodifluoromethane", *Kogyo Kagaku Zasshi*, Vol. 68, No. 10, 2002 (1965). The studies were conducted exclusively with high purity R-22 having a minimum specification of 99.3% $CHClF_2$, 0.4% $CCl_2F_2$ and 0.3% air. These earlier studies were not performed on contaminated refrigerant mixtures having unacceptably high levels of unwanted other refrigerant. Instead, the refrigerant used was new reactant (refrigerant) having allowable trace amounts of other refrigerant. Such "new" refrigerant would not require purification for removing other refrigerant in order to be used in air conditioning and refrigeration applications because the level of "other refrigerant" is well within recognized 0.5 percent standard of purity for use as is.

Hayashi's studies entailed the step of feeding R-22 in a gaseous state through aqueous solutions of sodium hydroxide. Using this gas-liquid phase reaction Hayashi was able to achieve only a low level of conversion of the pure R-22 gaseous refrigerant, hydrolyzing from about 1.50% to under 10% of the refrigerant feed for the duration of the runs. In sum, Hayashi began his studies with essentially 100 percent pure new R-22 refrigerant in a gas-liquid phase reaction.

Hayashi achieved a low level of conversion of the refrigerant present and never considered recovering a primary refrigerant which was sufficiently pure for recycling or reuse. Hayashi's stated purpose for conducting the experiments was to determine the organic products produced by the hydrolysis of R-22. The author concluded from his studies, that formate was the only organic product produced.

In addition to not achieving a quantitative destruction of R-22 in a gas-liquid phase reaction, and not achieving a purification between two or more refrigerants because only a single refrigerant was present, Hayashi failed to recognize the presence of undesirable secondary refrigerant by-products, such as trifluoromethane (R-23) generated in the hydrolysis of R-22 with strong aqueous base, how to avoid their formation, or how to eliminate them. In duplicating the hydrolysis reactions according to the methods of Hayashi we found significant amounts of other refrigerant by-product was generated, which actually contaminated the remaining unreacted R-22, rendering it unsuitable for further use as a refrigerant. Finally, Hayashi's paper reiterated what other researchers in the field, such as Jack Hine had previously discovered, namely that dichlorodifluoromethane (R-12) is not easily susceptible to being hydrolyzed, and that protonic hydrogen atom may make the hydrolysis of chlorodifluoromethane (R-22) easier.

The purification of non-refrigerant perfluorocarbons has been described in the literature. Unexamined German Offenlegungsschrift 42 05 341 to Meinert relates to the removal of residual non-refrigerant impurities consisting of compounds still containing hydrogen atoms and/or olefinic double bonds from the reactants employed in manufacturing the non-refrigerant perfluorocarbons. Meinert's methods were not employed in reclaiming used fluorocarbon compounds, but instead were employed as a final purification step in manufacturing medical/biological grades of perfluorodecalin, trifluorotributylamine commonly used as blood substitutes in carrying oxygen in red blood cells.

Meinert's methodology included a complicated sequence of reactions and manipulative steps involving the production of olefinic double bonded intermediates requiring the introduction of amine functionalities across the double bonds. Meinert's process was performed using secondary amines, strong base, calcium and barium ions and costly fluorinated surfactants in order to provide an emulsified homogeneous reaction mixture. According to Meinert, a double bonded structure is first formed by splitting off HF in the presence of KOH. A series of amine intermediates are prepared by reacting the double bonded compounds with HX where X is a secondary amine ($R_2N$—) and an alkoxide. A similar reaction is also taught with an acyclic structure fully fluorinated but for one hydrogen atom. The contaminants appear to be converted to higher boiling amides and amines. Reactions of Meinert were carried out at high temperatures in the range of 150° to 170° C., well above the critical temperatures of refrigerant compounds. At the completion of the reaction a lower perfluorocarbon phase develops, an intermediate aqueous phase containing dissolved alkoxide/alcohol, plus surfactant, and an upper amine phase. After filtering off solid products and separating the phases the perfluorocarbon is subjected to distillation.

Other known technologies for the destruction of CFCs such as thermal oxidation, catalytic decomposition, supercritical water oxidation, plasma destruction methods, biological processes, UV photolysis, and so on, are either in experimental stages of development, economically unattractive or incapable of selectively destroying the unwanted contaminating refrigerant without also eliminating the desired refrigerant.

Accordingly, there is need for more highly efficient and selective methods of purifying refrigerants contaminated with other unwanted refrigerants, and particularly refrigerants which become contaminated after manufacturing has been completed and have entered channels of commerce, such as becoming cross-contaminated after being used in some instances with difficult to remove small, but nevertheless, unacceptably high levels (>0.5 percent) of other refrigerants during collection and handling procedures. Such methods should be capable of purifying refrigerants contaminated with even very small amounts, e.g., between 0.5 and 2.0 percent of other refrigerant to provide essentially a quantitative destruction of unwanted other refrigerant(s), within practical time limits and do so without unwanted by-products appearing in the purified refrigerant. In addition, such methods should require a minimal number of steps without the need to form intermediates, nor require costly additives or final purification steps in connection with the removal of additives and reactants by washing the recovered primary refrigerant and/or requiring final distillation steps.

SUMMARY OF THE INVENTION

The term "refrigerant" as used throughout the specification and claims is a term intended to mean low boiling fluorocarbon compounds as a class of chemicals which are suitable principally for use in refrigeration and air conditioning equipment, but may have other applications. The term "refrigerant" embraces halofluorocarbons and halofluorohydrocarbons, such as chlorofluorocarbons (CFCs), bromofluorocarbons, chlorofluorohydrocarbons (HCFCs), and so on. Likewise, the term is also intended to include those fluorocarbon refrigerants which are useful as aerosol propellants, in manufacturing synthetic foams, packaging, insulation, and retardant compounds for fire extinguishers.

While the term "refrigerant" as discussed above is intended to encompass a rather extensive range of halofluorocarbon and halofluorohydrocarbon compounds, the term refrigerant for purposes of this invention is not open ended as to include any and all halofluorocarbon and halofluorohydrocarbon compounds. That is, the term "refrigerant" for this invention is not intended to include compounds not generally recognized as refrigerants by persons skilled in the art. For example, unexamined German Offenlegungsschrift 42 05 341 to Meinert infra. discloses methods for purifying perfluorocarbons and perfluorocarbon mixtures contaminated with impurities containing hydrogen and/or carbon to carbon double bonds. Generally, the compounds of Meinert are biocompatible compounds which find use in the fields of medicine, biology and microelectronics. Specific representative best mode examples of the compounds of Meinert are perfluorodecalin, perfluorotributylamine and perfluorooctane, all of which are not generally recognized in the field as low boiling "refrigerant" compounds, but are compounds employed, for example in medicine as biologically inert blood substitutes in carrying oxygen in red blood cells. Accordingly, the term "refrigerant" as appearing herein and in the appended claims is intended not to include fluorocarbon compounds either generally not classified as refrigerants in the literature, or which have utilities generally recognized by artisans as not normally associated with refrigerants, such as the blood substitutes of the Meinert patent publication.

More appropriately, it should be understood "refrigerant" as recited in the specification and claims is intended to embrace a range of compounds suitable mainly for air conditioning and refrigeration applications, plus some of the more commonly known applications, such as retardants in fire extinguishers. They include products commercially available under trademarks, such as Freon, Halon, Frigen, Arcton, Genetron and Isotron.

In accordance with the invention, an improved method is provided for the dehalogenation of contaminating refrigerants, and more particularly, halofluorohydrocarbon refrigerants. It is a principal object of the invention to provide useful methods of purifying fluorocarbon compositions which allow for the selective destruction of contaminating refrigerants and recycling or reuse of commercially important refrigerants.

The purification methods disclosed herein include the steps of:

(a) providing a composition comprising at least two refrigerants (i) a perhalogenated refrigerant compound and (ii) a contaminating fluoroalkane refrigerant compound having at least one hydrogen atom and at least one other halogen atom in addition to fluorine, e.g. chlorine, bromine and/or iodine;

(b) reacting the composition of step (a) with an aqueous solution of a base to selectively decompose the contaminating fluoroalkane refrigerant compound (ii), and (c) recovering the refrigerant composition from the reaction mixture of step (b), the composition comprising the perhalogenated refrigerant compound (i), the recovered composition being sufficiently free of the contaminating fluoroalkane refrigerant compound (ii) to enable recycling/reuse.

Quite significantly, it was discovered that refrigerant mixtures, like azeotropes, such as dichlorodifluoromethane contaminated with chlorodifluoromethane, and other refrigerant mixtures which are not azeotropes but have similar boiling points thereby making separation by distillation difficult, can be effectively purified and separated by methods disclosed herein. The separated and recovered refrigerants meet ARI 700 specifications making them suitable for reuse.

As a further aspect of the invention methods are provided for purifying refrigerant compositions by the steps of:

(a) providing a composition comprising at least two refrigerants: (i) a refrigerant selected from the group consisting of an azeotrope and a mixture of refrigerants having similar boiling points and (ii) a contaminating fluoroalkane refrigerant compound having at least one hydrogen atom and at least one other halogen atom in addition to fluorine;

(b) reacting the composition of step (a) with an aqueous solution of a base to selectively decompose the contaminating fluoroalkane refrigerant compound (ii), and (c) recovering the refrigerant composition from the reaction mixture of step (b), the refrigerant composition comprising the azeotrope or mixture of refrigerants having similar boiling points (i), the recovered composition being sufficiently free of said contaminating refrigerant compound (ii) to enable recycling/reuse.

The invention also contemplates as a further embodiment the purification of commercially available azeotropic refrigerant mixtures which have become contaminated with excess amounts of undesirable halofluorohydrocarbon components, after production and entry into channels of commerce. For example, the commercially available azeotropic refrigerant R-502 comprising a mixture of 51 percent R-115 (chloropentafluoroethane) and 49 percent R-22 may become inadvertently contaminated during handling with additional R-22, to produce a non-usable mixture. Accordingly, the methods of the present invention enable the reduction in the level of unwanted R-22 as to provide a reusable azeotropic refrigerant composition which meets new refrigerant specifications for other refrigerant. The present invention is noteworthy in providing a useful means for altering portions of a refrigerant mixture without total elimination.

The invention is especially useful in the purification of refrigerants which have become contaminated after being manufactured and have entered channels of commerce. They include, for instance, the treatment of "used" refrigerants, which are defined in greater detail below. Such refrigerants may include those, for example, collected from air conditioning and refrigeration equipment during servicing or those recovered in recycling used equipment, e.g. refrigerators, automobiles, etc., taken out of service, wherein refrigerant removed from a sealed system is inadvertantly or otherwise contaminated with other refrigerants. This method of purification includes the steps of:

(a) introducing an aqueous solution of a base into a closed vessel, wherein the base is preferably one recognized as a strong base, like sodium hydroxide;

(b) introducing into the closed vessel of step (a) a "used" refrigerant composition comprising (i) a primary perhalogenated refrigerant compound and (ii) a contaminating fluoroalkane other refrigerant compound in an amount >0.50 percent-by-weight. The other refrigerant compound will typically have at least one hydrogen atom and at least one other halogen atom in addition to fluorine. The refrigerant composition present in the closed vessel is principally in a liquid state, forming a liquid-liquid phase heterogeneous reaction mixture with the aqueous base. The headspace of the closed vessel may contain refrigerant in a gaseous state. The reaction is under elevated pressure;

(c) the liquid-liquid heterogeneous reaction mixture is mixed in the closed vessel at a temperature below the critical temperature of the refrigerant composition to maintain the refrigerant composition principally in a liquid state. The "critical temperature" or critical point is intended to mean the transition point above which the refrigerant composition is in a gaseous state and cannot be reliquified by autogenous pressure alone. The base reacts with the contaminating fluoroalkane other refrigerant of the heterogeneous reaction mixture to selectively decompose only the contaminating refrigerant. The base is present in the reaction mixture in a sufficient amount to enhance the rate of reaction and achieve a quantitative decomposition of the contaminating fluoroalkane other refrigerant, and (d) the primary perhalogenated refrigerant (i) is recovered from the heterogeneous liquid-liquid phase reaction mixture of step (c) with a sufficiently reduced amount of contaminating fluoroalkane other refrigerant (ii) as to enable recycling or reuse in refrigeration or air conditioning equipment. This means the recovered primary refrigerant will generally contain <0.5 percent-by-weight other refrigerant. The purified primary refrigerant can be efficiently recovered as a gaseous product, where it can be compressed to reliquify, and packaged for reuse.

As previously indicated, the primary refrigerant (i) is a halofluorocarbon compound, e.g., chlorofluorocarbon refrigerant, bromofluorocarbon refrigerant, and the contaminating fluoroalkane refrigerant (ii) is generally a halofluorohydrocarbon compound, e.g., chlorofluorohydrocarbon.

DESCRIPTION OF THE PREFERRED EMBODIMENTS

Methods of the invention encompass the purification of compositions containing useful primary refrigerants.

Expressions such as "primary refrigerant" and "primary perhalogenated refrigerant" as disclosed and claimed herein are used to denote the specific refrigerant(s), according to the definition for the term "refrigerants" as previously provided, and designates those particular compounds desired for recovery in the purification process from refrigerants which have become contaminated with other refrigerants. Primary refrigerants include mainly refrigerants which are perhalogenated, or in other words, refrigerant compounds in which all the carbons are fully substituted with halogen atoms. They include such representative examples as Freon® 11 (fluorotrichloromethane), Freon 12 (dichlorodifluoromethane), Freon 13 (chlorotrifluoromethane), Freon 14 (tetrafluoromethane), Freon 13B1 (bromotrifluoromethane), and so on.

The expression "other refrigerant" is used herein to denote the contaminating refrigerant to be eliminated from refrigerant compositions containing the primary refrigerant. The methods are especially useful in purifying previously used refrigerant compositions contaminated with >0.5 percent-by-weight of other refrigerant. Primary refrigerant compositions through post manufacturing processes, such as through collection and handling can become contaminated with other refrigerants, particularly fluoroalkane refrigerant compounds having at least one hydrogen atom and at least one halogen atom in addition to their fluorine atom(s), which halogen atoms may be chlorine, bromine and/or iodine.

The term "fluoroalkane" is intended to include mainly fluoromethane type refrigerant compounds, but also fluoroethanes. Specific representative examples of fluoromethane type other refrigerants include, but are not limited to FC-21 (fluorodichloromethane), FC-22 (chlorodifluoromethane), FC-21B1 (bromochlorofluoromethane), etc. Other fluoroalkane refrigerants include, for instance, 1,1,2,2-tetrachloro-2-fluoroethane (FC-121); 1,1,1-trifluoro-2,2-dichloroethane (FC-123).

As previously mentioned, the invention relates principally to the purification of "refrigerant compositions" comprising primary refrigerants which have become contaminated with sufficient levels of other refrigerants as to render the compositions unsuitable for use in air conditioning or refrigeration equipment, typically >0.5 percent-by-weight other refrigerant. The invention concerns contamination of the primary refrigerant after manufacturing of it has been completed and the primary refrigerant has entered commercial trade channels. In this regard, one mode of other refrigerant contamination of primary refrigerants which the inventors found occurring takes place when refrigerants are being removed from air conditioning and refrigeration equipment during servicing and recycling of such equipment, and the used refrigerant collected in common vessels/cylinders. Contamination of collected used primary refrigerants, such as R-12, occurs when service personnel inadvertantly or otherwise collect two or more chemically dissimilar refrigerants in a common collection vessel intended for, but a single grade of refrigerant, thereby contaminating the primary refrigerant, e.g. R-12 with seemingly minor, but unacceptably high levels, i.e. >0.5 percent of other refrigerant, e.g., R-22.

Used primary refrigerants once purified according to the methods disclosed and claimed herein meet standards of purity for other refrigerants for reuse in air conditioning and refrigeration equipment, and are virtually 100 percent primary refrigerant, but for trace amounts of other refrigerant, normally <0.5 percent-by-weight.

Expressions such as "used refrigerant" or "used refrigerant compositions" are intended to denote primary refrigerants which have been manufactured, purified and packaged for sale as refrigerant material with <0.5 percent other refrigerant content for entry into commercial trade channels as new material, but through handling and/or utilization become contaminated with levels of other refrigerant materials rendering them unacceptable for reuse in refrigeration or air conditioning equipment without prior purification. Generally, used refrigerant material contains >0.5 percent other refrigerant and fails to meet other refrigerant content specifications, such as ARI 700 requirements.

The methods of purification of the present invention are useful in treating refrigerant compositions containing from between 0.5 and 80 percent-by-weight other refrigerant. However, the methods are especially noteworthy in their ability to effectively and efficiently purify refrigerant compositions contaminated with difficult to remove minor, but nevertheless unacceptably high levels of unwanted other refrigerants present generally between 0.50 and about 1.0 or 2.0 percent-by-weight where reactions normally would be expected to proceed at slow rates because of low concentration of reactants. Yet, surprisingly and unexpectedly the purification methods of the invention provide for quantitative destruction of unwanted other refrigerant all within practical time limits, usually within hours, and not days to provide a primary refrigerant which meets not less than minimum specifications for other refrigerant content.

The recovered primary refrigerant not only meets the foregoing specifications of purity for other refrigerant within practical time limits as previously discussed, but does so without unwanted by-products appearing in the final purified refrigerant material. Without being held to any theory or exact understanding of the path or mode of action occurring in the case of the reactions of the present invention, it is nevertheless believed the manipulative steps and/or process conditions, as discussed in greater detail below, contribute to the production of purified primary refrigerants without the build-up of undesirable secondary refrigerant by-products, such as trifluoromethane. As previously indicated, the present inventors discovered that unwanted contaminating refrigerant by-products are often generated, knowingly or otherwise, during hydrolysis reactions of refrigerants with aqueous solutions of strong bases. The generation of such refrigerant by-products can effectively render hydrolysis reactions with base useless as a means for purification.

For example, in duplicating the hydrolysis reactions of Hayashi supra, in which R-22 in a gaseous state was bubbled through a dilute aqueous solution of sodium hydroxide unacceptably high levels of unwanted R-23 were found in the refrigerant. In addition to employing a gas-liquid phase reaction, this earlier process conducted the hydrolysis reaction in an unpressurized open vessel. Hayashi's methodology achieved only a low rate of conversion of the R-22 present while generating an unacceptable high level of R-23 refrigerant by-product. Hence, based on the foregoing findings, it could be concluded that such earlier known reactions of refrigerants with aqueous solutions of strong base would be unsuitable for purifying refrigerants contaminated with halofluorohydrocarbon refrigerants, such as R-22.

Notwithstanding the foregoing results, it was discovered the objectives of the present invention are met by conducting the reaction in a closed vessel, generally under elevated pressure, which means above atmospheric pressure, and more particularly, at least under sufficient autogenous pressure to maintain the refrigerant in a liquid state. The aqueous solution of base is mixed with the contaminated refrigerant composition in the reaction vessel, the latter being predominantly as a liquid, and not as a gas. Refrigerant gas may, however, exist in the headspace of the reactor. Thus, instead of forming a gas-liquid reaction mixture with the aqueous solution of strong base, the bulk of the refrigerant consists of a liquid which is mixed with the solution of strong base to form an intimate heterogeneous liquid-liquid phase reaction mixture.

Generally, the base is present in an amount which is sufficient to enhance the rate of decomposition of the other refrigerant. Preferably, this includes excess amounts of base relative to the refrigerant composition. Typically, the reaction mixture contains an amount of base ranging from 1.05 to about 1.5 times the stoichiometric amount required to decompose the halofluorohydrocarbon other refrigerant. Emulsifiers, surfactants, metal cations, such as barium and calcium ions to achieve miscibility in an otherwise multi phase system, are neither required nor desirable since they only detract from the economics of the process.

More significantly, such additives constitute foreign substances being introduced into the purification reaction mixture and will appear as undesirable contaminants in the final primary refrigerant product. Accordingly, they too will have to be removed by further purification steps in order to provide a primary refrigerant of suitable purity for reuse in air conditioning or refrigeration equipment. Similarly, the methods of the invention do not require splitting off HF to form double bonded structures, or the introduction of amines for purposes of preparing intermediates with the other refrigerant. Accordingly, the present invention provides for achieving a high degree of purity without performing a series of complex intermediate reactions, or the introduction into the reaction mixture of contaminating substances. In addition, the improved methods do not result in a final primary refrigerant containing unwanted refrigerant by-products, such as R-23. By conducting the reaction in a closed vessel under at least autogeneous pressure conditions, at temperatures below the critical temperature of the refrigerant mixture, preferably in the presence of an excess amount of base, any unwanted refrigerant by-product formed in the process, such as trifluoromethane are not found in the final products. The methods of the prior art neither recognize the potential for producing unwanted refrigerant by-products, nor do they teach how to eliminate them from appearing in the final recovered primary refrigerant.

Another principal objective of the invention is the selective chemical decomposition of other refrigerants in compositions of refrigerant mixtures without decomposing the primary refrigerant. The invention comprises as a further principal objective the steps of separation and recovery of the composition containing the primary refrigerant from an aqueous reaction medium in a refined or purified state free or virtually free of other refrigerant, so as to meet American Refrigeration Institute specifications for other refrigerants. The methods enable recycling/reuse of discontinued or potentially scarce refrigerant compounds.

While the methods of the invention are especially useful in the reclamation of contaminated perhalomethane type primary refrigerants the invention contemplates the purification and recovery of other perhaloalkane primary refrigerants as well, such as the fluoroethanes and fluorobutanes. Representative examples include fluorocarbon or FC-112 (1,1,2,2-tetrachloro-1,2-difluoroethane), FC-113 (1,1,2-trichloro-1,2,2-trifluoroethane), and the like.

In addition to the reclamation of refrigerant compositions comprising a single perhalogenated primary refrigerant contaminated with other refrigerant(s), the invention contemplates the purification of refrigerant mixtures having similar boiling points, and particularly azeotrope refrigerants, like Freon 500 (dichlorodifluoromethane and 1,1-difluoroethane), Freon-503 (trifluoromethane and chlorotrifluoromethane), and particularly an azeotrope of dichlorodifluoromethane in which chlorodifluoromethane is the other refrigerant. In addition to the foregoing, the methods disclosed herein include the purification of commercially available azeotropic mixtures containing excessive amounts of halofluorohydrocarbon (HCFC) refrigerant, e.g., chlorodifluoromethane, which can be reduced to specification levels to enable reuse of the azeotropic mixture for refrigeration and air conditioning applications. In this regard, the contaminated azeotropic refrigerant mixture is reacted with sufficient amounts of base in aqueous solution needed to only lower the level of the halofluorohydrocarbon, utilizing the reaction conditions described herein. The purified used azeotropic refrigerant mixture meets new refrigerant specifications.

The purification methods provide for the step of reacting a primary refrigerant-containing composition contaminated with other refrigerant, with an aqueous solution of a base to selectively decompose the contaminating other refrigerant. The expression "aqueous solution of a base" or variations similar thereto, as used in the specification and claims is intended to mean virtually any base having $pK_b$ in a range from about <0 to 7 wherein the base is the solute and water is the solvent therefor. The expression is not intended to include solutions of base wherein water is present in only minor amounts or present as an impurity. In practice, the aqueous solutions of base typically contain from about 3 to about 25 percent by weight base for those bases which are solids prior to dissolution. On the other hand, for bases which are liquids prior to mixing with water, aqueous solutions of bases can be prepared having considerably higher concentrations, i.e, up to about 95 percent. Representative examples of stronger bases at the lower end of the $pK_b$ range include alkali metal hydroxides, e.g., sodium, potassium and lithium hydroxides; alkaline earth metal hydroxides, e.g., calcium and magnesium hydroxides, and mixtures of metal hydroxides. Representative examples of weaker bases at the upper end of the $pK_b$ range include alkali metal and alkaline earth metal carbonates and bicarbonates, such as sodium, potassium, calcium and magnesium carbonates, bicarbonates and mixtures thereof. Other representative examples of useful bases are the quaternary ammonium bases, like tetramethylammonium and cetyltrimethylammonium hydroxides.

The reaction of the heterogeneous liquid-liquid reaction mixture comprising the aqueous solution of base with the contaminated refrigerant composition comprising primary and other refrigerant(s) in a liquid state in the reactor is performed in a closed pressure vessel at temperatures below the critical temperature of the refrigerant mixture. This includes temperatures generally in the range of between about 0° and 100° C.; more specifically, in the range of about 5° C. to about 80° C., and more optimally from about 30° to about 70° C. At temperatures below 0° C. the rate of reaction of other refrigerant and base becomes reduced.

The process may be either batch or continuous. Conducting the reaction with an aqueous solution of a base, potassium hydroxide for instance, results in the formation of such by-products as potassium formate, potassium salts of fluorine, chlorine, bromine and iodine, depending on the particular other refrigerant present. Advantageously, salt by-products of the purification reaction, such as potassium fluoride, potassium chloride and potassium formate, are only soluble in the aqueous phase of the reaction mixture allowing for recovery of a purified refrigerant composition containing primary refrigerant substantially free of other refrigerants, and other unwanted by-products, like the salts previously mentioned.

Significantly, it was found that a "clean" separation and recovery of the primary refrigerant-containing composition from the aqueous reaction mixture is achieved by withdrawing the primary refrigerant from the reaction vessel in a gaseous state. The withdrawn refrigerant can be dried, compressed and finally packaged for storage, etc. Alternatively, the reaction mixture may be allowed to remain in a quiescent state after mixing. With completion of the decomposition reaction the reactor mixer is deactivated. Advantageously, the limited miscibility of the primary refrigerant-containing composition in the aqueous solution of base allows the reaction mixture to separate into two distinct liquid phases, e.g., an upper aqueous phase, and lower refrigerant phase containing the primary refrigerant. This enables separation and recovery of the primary refrigerant-containing composition to be especially convenient where in most instances the need for further processing to recover substantially pure primary refrigerant can be avoided. That is, it was found, for example, the lower refrigerant phase can be readily separated from the upper aqueous layer or phase by withdrawing as a liquid from the bottom of the reaction vessel. Any residual solid salt by-products in the lower refrigerant phase can be removed by means of an in-line filtration device of known design.

As a further aspect of the inventive process, it was discovered that dehalogenation of other refrigerants results in formation of reaction by-products, like sodium formate, sodium chloride and sodium fluoride. As the other refrigerant is dehalogenated base is depleted from the reaction mixture, and must be replenished. Simultaneously, reaction by-products are building-up in the aqueous reaction mixture. Although sodium fluoride is relatively insoluble in the aqueous reaction mixture, sodium formate and sodium chloride are fairly soluble, making separation of a large portion of the by-products from the aqueous phase of the reaction mixture more difficult.

However, it was found that by adding sodium hydroxide, for instance, to the aqueous phase of the reaction mixture to replenish the base, the greater solubility of the sodium hydroxide in water causes the less soluble salt by-products, i.e., formates, fluorides, bromides, chlorides, etc., to salt-out or precipitate from the "heel" of the reactor. Hence, it has been found that the reactor by-products can be conveniently and efficiently separated from the aqueous reaction mixture by means of replenishing the aqueous solution of base. Removal of the precipitated salts in turn can be effectuated by filtration means using methods within the purview of one having ordinary skill in the art.

The following specific examples demonstrate the various embodiments of the invention, however, it is to be understood they are for illustrative purposes only and do not purport to be wholly definitive as to conditions and scope.

EXAMPLE I

In order to demonstrate the recovery of perhalogenated CFCs from a mixture of refrigerants, a laboratory scale purification system was assembled. The system included a reactor consisting of a 14 liter stainless steel autoclave fitted with inlets/outlets to permit the addition of reactants and removal products. Vaporized products were withdrawn from the head space at the upper portion of the reactor, whereas liquid phases were withdrawn from outlets in the central and lower regions of the reactor. The reactor was equipped with a 1725 rpm Lignin mixer driving a 3 inch, 3 blade propeller with the stirrer shaft entering the reactor through a seal at the top of the reactor. A sight glass provided visual inspection of the reactor contents. Reactor temperature was regulated by an external jacket.

The reactor was evacuated and the vacuum used to draw in 7.1 liters of a 12.5 percent by weight aqueous solution of sodium hydroxide. A refrigerant mixture was analyzed according to ARI standard 700-93 specification using a Hewlett-Packard HP 5840A gas chromatograph and thermal conductivity detector. The refrigerant mixture was found to consist of 95.27 percent dichlorodifluoromethane (R-12), 4.45 percent chlorodifluoromethane (R-22), 0.11 percent air and 0.17 percent other impurities.

The contents of the reactor were stirred and cooled to $-7.3°$ C. by means of a mixture of dry ice and isopropanol in the reactor jacket. This permitted direct transfer of the above mixed liquid refrigerant from the storage cylinder to the reactor by pressure difference. By the time the addition was complete the reactor had cooled further to $-11°$ C. The coolant from the reactor jacket was drained and replaced with hot water, bringing the reactor to a maximum temperature of $38°$ C. and pressure of 138 psig during the run. When the reactor contents reached $25°$ C., one half hour after the refrigerant addition was complete, the time was noted.

Samples were collected at 15 minute intervals (actual stirring time). Sample collection procedure consisted of stopping the stirrer and allowing the reaction mixture to separate into a liquid refrigerant phase at the bottom of the reactor, and an upper aqueous liquid phase above the lower refrigerant phase, and then withdrawing a sample of the liquid refrigerant phase from the bottom of the reactor. This protocol was performed to obtain a more accurate and representative sampling of the treated refrigerant composition. Until the R-22 refrigerant level was reduced to specification levels of <0.5 percent the reaction was allowed to continue. This method also isolated the more volatile R-22 vapor in the head space of the reactor keeping it from recontaminating the liquid refrigerant phase at the bottom of the reactor, and thereby functioned as a barrier. In addition, caustic soda in the intermediate aqueous phase provided a further useful function by dehalogenating R-22 refrigerant in the upper vapor phase which might have liquefied and recontaminate the refrigerant phase at the bottom of the reactor.

TABLE 1

| Time (minutes) | R-22 (%) |
| --- | --- |
| 15 | 1.85 |
| 30 | 0.85 |
| 60 | 0.17 |

The final analysis of the refrigerant phase at 60 minutes into the run showed ARI 700 specifications for other refrigerants being met with R-12=99.57 percent; R-22 other refrigerant=0.17 percent; air, water and other trace impurities=0.26 percent.

EXAMPLE II

A further experiment was conducted with the same refrigerant mixture used in Example I. The reactor was evacuated and the vacuum applied to withdraw 7.1 liters of 12.5 percent of the aqueous sodium hydroxide solution. The reaction was conducted using the same system as in Example I, except the refrigerant mixture (10.5 pounds) was charged to the reactor with an Applied Research Laboratories ReKlame® refrigerant recovery and recycle system. The refrigerant was withdrawn from the cylinder and added to the reactor as a liquid. Hot water was added to the reactor jacket, heating reactor contents to 42° C., and at a reactor pressure of 145 psig. After addition of the refrigerant mixture was completed the stirrer was deactivated, and the reaction mixture allowed to settle into a lower liquid refrigerant phase and an upper or intermediate aqueous phase. A refrigerant sample was withdrawn from the bottom of the reactor, and the reaction was allowed to continue for a period of one hour with additional samples withdrawn in the same manner from the same phase at 15 minute intervals and analyzed for other refrigerant. The analyses are provided in Table 2 below:

TABLE 2

| Time (minutes) | R-22 (%) |
|---|---|
| 0 | 1.87 |
| 15 | 0.60 |
| 30 | 0.11 |
| 45 | 0.02 |
| 60 | <0.01 |

The final analysis of the refrigerant phase at 60 minutes into the run showed ARI 700 specifications for other refrigerants being met with R-12=99.01 percent; R-22 other refrigerant=<0.01 percent; air, water and other trace impurities 0.98 percent.

EXAMPLE III

In order to demonstrate the performance of the purification methods of the invention relative to studies published in a paper entitled "Preparation of Sodium Formate by Hydrolysis of Chlorodifluoromethane" by Takao Hayashi supra., and the Unexamined German Offenlegungsschrift 42 05 341 to Meinert, a series of experiments were conducted.

In setting up appropriate experiments which were suitably representative of the above publications reactant feed mixtures of perfluorocarbon compounds were used which also contained some other carbon compound having hydrogen and fluorine atoms. While the disclosures of Meinert did not relate to the purification of refrigerants which have become contaminated with other refrigerant compounds, refrigerant compound containing other refrigerants were employed. The experiments corresponding to those of Hayashi were also performed with compounds classified as refrigerants, namely chlorodifluoromethane (R-22) containing trace amounts of dichlorodifluoromethane (R-12). The refrigerant of Hayashi was also employed because it more closely paralleled the refrigerant mixtures being treated according to the instant invention than the biologically inert perfluorinated compounds of Meinert.

A 2.62 molar aqueous solution of sodium hydroxide, as employed by Hayashi, was placed in 2 liter Erlenmeyer flasks. Because the best results achieved by Hayashi in hydrolyzing his refrigerant composition with aqueous base resulted in consuming only 9.4 percent of the R-22, a train of five (5) such 2 liter Erlenmeyer flasks were connected in series to simulate a cascading reaction train as needed for a commercial-like purification process. Refrigerant gas was fed to the first reaction flask would react with the aqueous sodium hydroxide, and would then be sent to the next flask containing aqueous sodium hydroxide, and so on. The flasks were fitted with 40–60 micron fritted gas dispersion tubes. Septa in the inlet and outlet tubing permitted sampling of the respective gases for purposes of analysis.

The experiment ran for six (6), one (1) hour intervals with gas samples from each flask taken sequentially for analysis at 10 minute intervals beginning with the second hour, so that during each one hour period a gas sample was taken from each of the five flasks, and repeated the third hour of the run, and so on.

In order to emulate the methods specifically disclosed by the publications, and particularly the methods of Hayashi which disclose hydrolyzing chlorodifluoromethane (R-22) with trace amounts of other refrigerant, like R-12 (dichlorodifluoromethane) the feed gas employed in the experiments profiled closely that of Hayashi. A refrigerant gas was used from a new 30 pound cylinder of Elf Atochem Forane® 22 brand of chlorodifluoromethane which contained mainly R-22 (99.7 percent), but also contained small amounts of other refrigerants, namely R-23 (trifluoromethane), R-12 (dichlorodifluoromethane) and R-142(b) (1-chloro-1, 1-difluoroethane).

ANALYSIS OF GAS SAMPLES

In replicating the methods of the publications the starting feed gas and treated gases (unreacted feed plus any volatile reaction products formed during the reaction) were analyzed using a Hewlett Packard Model 5890, Series 2 gas chromatograph equipped with a flame ionization detector to monitor the reaction. In addition, samples were analyzed by an independent laboratory, Integral Sciences Incorporated, Columbus, Ohio. Integral Sciences performed independent analyses using a Varian 3700 chromatograph with a flame ionization detector and with retention times correlated to refrigerant standards. Peak identity was confirmed by analysis on a Fisons Model 8000 gas chromatograph with a Model 800 mass spectrometer.

TABLE 3

COMPOSITION OF GASES TREATED ACCORDING TO THE PUBLICATIONS

| | Percent Starting Material | PERCENT OF REFRIGERANT REMAINING | | | | |
|---|---|---|---|---|---|---|
| | | Flask 1 | Flask 2 | Flask 3 | Flask 4 | Flask 5 |
| HOUR 2 | | | | | | |
| R-23 | 0.0131 | 0.619 | 1.26 | 1.93 | 2.53 | 2.73 |
| R-22 | 99.7 | 99.0 | 98.2 | 97.1 | 96.2 | 85.6 |
| R-12 | 0.0033 | 0.0407 | 0.0982 | 0.237 | 0.376 | 0.664 |
| R-142b | 0.270 | 0.335 | 0.482 | 0.682 | 0.842 | 0.953 |

*TOTAL "OTHER REFRIGERANTS" REMAINING AFTER 1 HOUR . . . 3.683%
Sampling began 1 hour after commencing
*Includes R-23 and R-142b only

| HOUR 3 | | | | | | |
|---|---|---|---|---|---|---|
| R-23 | 0.0131 | 0.457 | 1.64 | 1.64 | 2.72 | 3.20 |
| R-22 | 99.7 | 99.0 | 97.8 | 97.7 | 96.3 | 95.6 |
| R-12 | 0.0033 | — | 0.0289 | 0.0383 | 0.0782 | 0.127 |
| R-142b | 0.270 | 0.463 | 0.545 | 0.605 | 0.884 | 1.04 |

TOTAL "OTHER REFRIGERANTS" REMAINING AFTER 2 HOUR . . . 4.24%

| HOUR 4 | | | | | | |
|---|---|---|---|---|---|---|
| R-23 | 0.0131 | 0.826 | 2.22 | 3.81 | 4.28 | 4.82 |
| R-22 | 99.7 | 98.8 | 97.2 | 95.2 | 94.5 | 93.7 |
| R-12 | 0.0033 | 0.0072 | 0.0143 | 0.0380 | 0.0617 | 0.124 |
| R-142b | 0.270 | 0.342 | 0.587 | 0.967 | 1.11 | 1.30 |

TOTAL "OTHER REFRIGERANTS" REMAINING AFTER 3 HOUR . . . 6.12%

TABLE 3-continued

COMPOSITION OF GASES TREATED ACCORDING TO THE PUBLICATIONS

| | Percent Starting Material | PERCENT OF REFRIGERANT REMAINING | | | | |
|---|---|---|---|---|---|---|
| | | Flask 1 | Flask 2 | Flask 3 | Flask 4 | Flask 5 |
| HOUR 5 | | | | | | |
| R-23 | | 0.0131 | 0.712 | 1.82 | 2.93 | 2.38 | 3.67 |
| R-22 | | 99.7 | 98.9 | 97.7 | 96.3 | 96.9 | 95.3 |
| R-12 | | 0.0033 | 0.0047 | 0.0075 | 0.0122 | 0.0147 | 0.0301 |
| R-142b | | 0.270 | 0.330 | 0.509 | 0.721 | 0.700 | 0.961 |

TOTAL "OTHER REFRIGERANTS" REMAINING AFTER 4 HOUR . . . 4.631%

| HOUR 6 | | | | | | |
|---|---|---|---|---|---|---|
| R-23 | 0.0131 | 1.09 | 2.62 | 3.92 | 5.09 | 6.46 |
| R-22 | 99.7 | 98.6 | 97.2 | 95.3 | 94.0 | 92.3 |
| R-12 | 0.0033 | 0.0047 | 0.0069 | 0.0115 | 0.0160 | 0.0291 |
| R-142b | 0.270 | 0.337 | 0.482 | 0.737 | 0.926 | 1.16 |

TOTAL "OTHER REFRIGERANTS" REMAINING AFTER 5 HOUR . . . 7.62%

As part of these studies an additional experiment was conducted to compare the methods of purification of refrigerants according to the present invention with those of the foregoing publications. The following protocol was followed:

A single reactor was set-up for a batch process run and charged with 535 pounds of a 28 percent aqueous solution of sodium hydroxide. The reactor was then charged with 400 pounds of a used refrigerant mixture consisting of refrigerants which had become contaminated with other used refrigerants during the collection process. The used refrigerant mixture consisted of a primary perhalogenated refrigerant compound, namely dichlorodifluoromethane (R-12) which was the desired refrigerant to be recovered, and several contaminating other refrigerants, mainly chlorodifluoromethane (R-22), plus small amounts of other refrigerants contained in the R-12 and R-22. Specifically, the starting used refrigerant mixture consisted of the following composition which was determined using the foregoing analytical equipment.

STARTING USED REFRIGERANT MIXTURE

| Refrigerant | Percent |
|---|---|
| R-12 | 88.360 |
| R-22 | 11.490 |
| R-23 | 0.002 |
| R-152a | 0.002 |
| R-115 | 0.096 |
| R-114 | 0.039 |
| R-11 | 0.004 |
| | 99.993 |

Before purification the above starting used refrigerant contained a total of 11.633 percent unwanted contaminating other refrigerant compounds in the R-12 (primary refrigerant). "Other refrigerant" included all refrigerants other than R-12. The analysis was performed using a gas chromatograph as described above in connection with the testing of the refrigerants of the publications. The 400 pounds of refrigerant was charged to the reactor containing the aqueous sodium hydroxide solution and agitated while the reaction took place. After 11 hours, agitation was terminated and the refrigerant from the reactor was withdrawn and analyzed according to the methods previously described. The used refrigerant treated according to the immediate invention had the following analysis:

PURIFIED USED REFRIGERANT

| Refrigerant | Percent |
|---|---|
| R-12 | 99.806 |
| R-22 | 0.016 |
| R-23 | 0.003 |
| R-152a | 0.002 |
| R-115 | 0.099 |
| R-114 | 0.063 |
| R-11 | 0.011 |
| | 99.937 |

The total contaminating "other refrigerant" present after treatment according to the claimed invention was 0.194 percent-by-weight.

TABLE 4

(INVENTION METHOD)

| Refrigerant | % Before Treatment | % After Treatment |
|---|---|---|
| R-12 | 88.36 | 99.806 |
| R-22 | 11.49 | 0.016 |
| R-23 | 0.002 | 0.003 |
| R-152a | 0.002 | 0.002 |
| R-115 | 0.096 | 0.099 |
| R-114 | 0.039 | 0.063 |
| R-11 | 0.004 | 0.011 |

TABLE 5

(INVENTION METHOD)

| | % Before Treatment | % After Treatment |
|---|---|---|
| Unwanted other refrigerant | 11.633% | 0.194% |

The numerical data of TABLE 1 of this Example III relating to the methods of the publications (Takao Hayashi) and Meinert most closely related to the instant invention showed a consistently higher level of unwanted "other refrigerants" remaining, including R-22 and R-23, far exceeding ARI (American Refrigeration Institute) 700 standards (<0.50 %) for refrigerants for recycling/re-using, whereas the numerical data according to the claimed methods, as represented by Tables 2 and 3, above provided surprisingly significantly lower residual levels of other refrigerants within ARI 700 specifications for reusable refrigerants.

While the invention has been described in conjunction with specific examples thereof, they are illustrative only. Accordingly, many alternatives, modifications and variations will be apparent to persons skilled in the art in light of the foregoing description, and it is therefore intended to embrace all such alternatives, modifications and variations as to fall within the spirit and broad scope of the appended claims.

We claim:

1. A method of purifying a refrigerant composition, which comprises the steps of:

(a) introducing an aqueous solution containing between about 12.5 percent-by-weight and about 95 percent-by-weight of a base into a closed vessel;

(b) introducing into the closed vessel of step (a) a contaminated refrigerant composition comprising (i) a primary perhalogenated refrigerant compound and (ii) a contaminating fluoroalkane other refrigerant compound in an amount >0.50 percent-by-weight, said other refrigerant having at least one hydrogen atom and at least one other halogen atom in addition to fluorine, said refrigerant composition being present in said closed vessel principally as a liquid, forming a liquid-liquid heterogeneous reaction mixture with said aqueous base;

(c) mixing the liquid-liquid heterogeneous reaction mixture under elevated pressure and at temperatures below the critical temperature of the refrigerant composition to maintain said composition principally as a liquid to selectively decompose said contaminating fluoroalkane other refrigerant compound (ii), said base being present in said reaction mixture in a sufficient amount to enhance the rate of decomposition of said contaminating fluoroalkane other refrigerant, and (d) recovering the primary perhalogenated refrigerant (i) from the heterogeneous liquid-liquid reaction mixture of step (c) with a sufficiently reduced amount of contaminating fluoroalkane other refrigerant (ii) <0.5 percent-by-weight and without the introduction of disqualifying by-product to enable recycling or reuse in refrigeration or air conditioning equipment.

2. The purification method of claim 1 wherein the primary refrigerant (i) is a halofluorocarbon and the contaminating fluoroalkane refrigerant (ii) is a halofluorohydrocarbon.

3. The purification method of claim 2 wherein the halofluorocarbon is a chlorofluorocarbon refrigerant and the halofluorohydrocarbon is a chlorofluorohydrocarbon refrigerant.

4. The purification method of claim 2 wherein said heterogeneous reaction mixture of step (c) is maintained at a temperature in a range from between about 0° and 100° C.

5. The purification method of claim 2 wherein said heterogeneous reaction mixture of step (c) is maintained at a temperature in a range from between about 30° and 70° C.

6. The purification method of claim 4 wherein said reaction mixture contains an excess amount of base relative to said contaminating halofluorohydrocarbon.

7. The purification method of claim 4 wherein said reaction mixture contains an amount of base ranging from 1.05 to about 1.5 times the stoichiometric amount required to decompose the halofluorohydrocarbon refrigerant present in the reaction mixture.

8. The purification method of claim 6 wherein said heterogeneous reaction mixture is under sufficient autogenous pressure to maintain the refrigerant composition in the closed vessel in a liquid state.

9. The purification method of claim 1 wherein the contaminating fluoroalkane other refrigerant (ii) contains from 1 to 3 carbon atoms.

10. The purification method of claim 1 wherein the contaminating fluoroalkane other refrigerant (ii) is a halofluoromethane type.

11. The purification method of claim 10 wherein the halofluoromethane other refrigerant is a member selected from the group consisting of chlorodifluoromethane, fluorodichloromethane, chlorofluoromethane, bromofluoromethane, bromodifluoromethane and mixtures thereof.

12. The purification method of claim 10 wherein said contaminated refrigerant composition comprises dichlorodifluoromethane contaminated with chlorodifluoromethane.

13. The purification method of claim 1 wherein the aqueous solution of a base is a hydroxide of a metal selected from the group consisting of alkali metals and alkaline earth metals.

14. The purification method of claim 1 wherein the contaminated refrigerant composition of step (b) comprises an azeotropic mixture.

15. The purification method of claim 1 wherein the contaminated refrigerant composition of step (b) comprises a mixture of at least two refrigerants having similar boiling points.

16. The purification method of claim 14 wherein the contaminated refrigerant composition of step (b) is an azeotropic mixture comprising dichlorodifluoromethane and chlorodifluoromethane, and the recovered refrigerant composition of step (d) comprises dichlorodifluoromethane.

17. The purification method of claim 14 wherein the azeotropic mixture is the primary refrigerant and the contaminating fluoroalkane other refrigerant is comprised of an excess amount of at least one of the refrigerants of said azeotropic mixture.

18. A method for purifying a contaminated refrigerant composition which includes (i) between about 20 percent-by-weight and about 99.5 percent-by-weight of at least one saturated $C_1$–$C_4$ perhalofluorocarbon, the molecular formula of said perhalofluorocarbon containing no hydrogen atoms but containing, in addition to carbon and at least one fluorine atom, at least one additional halogen atom selected independently from the group consisting of fluorine, chlorine and bromine, together with (ii) between about 0.5 percent-by-weight and about 80 percent-by-weight of at least one contaminating saturated $C_1$–$C_2$ fluoroalkane, the molecular formula of said fluoroalkane containing, in addition to carbon and fluorine, at least one hydrogen atom and at least one halogen atom selected from the group consisting of chlorine, bromine and iodine, which method comprises (a) producing a heterogeneous liquid/liquid reaction mixture by introducing the contaminated refrigerant composition into a pressurizable reaction vessel, along with a reagent which includes water and between about 12.5 percent-by-weight and about 95 percent-by-weight base in an amount sufficient to destroy the contaminating fluoroalkane;

(b) mixing and reacting the contents of the reaction vessel while controlling the temperature of the reaction mixture between about 0° C. and about 100° C. and adjusting the pressure in the reaction vessel to maintain the refrigerant composition in a predominantly liquid state for a period of time required to decontaminate the perhalofluorocarbon refrigerant; and (c) separating the aqueous phase from the decontaminated refrigerant phase and recovering the perhalofluorocarbon;

whereby the recovered decontaminated perhalofluorocarbon contains less than 0.5 percent-by-weight contaminating fluoroalkane.

19. The method of claim 18 wherein the period of time required to decontaminate the contaminated refrigerant composition is less than 24 hours.

20. The method of claim 18 wherein the perhalofluorocarbon is selected from the group consisting of fluorotrichloromethane, dichlorodifluoromethane, chlorotrifluoromethane, tetrafluoromethane, bromotrifluoromethane, 1,1,2,2-tetrachloro-1,2-difluoroethane, 1,1,2-trichloro-1,2,2-trifluoroethane, and mixtures thereof, and the contaminating fluoroalkane is selected from the group consisting of fluorodichloromethane, chlorodifluoromethane, bromochlorofluoromethane, 1,1,2,2-tetrachloro-2-fluoroethane, 1,1,1-trifluoro-2,2-dichloroethane, and mixtures thereof.

21. The method of claim 18 wherein the $pK_b$ of the base is between less than 0 and about 7.

22. The method of claim 18 wherein the base is selected from the group consisting of sodium hydroxide, potassium hydroxide, lithium hydroxide, calcium hydroxide, magnesium hydroxide, sodium carbonate, potassium carbonate, calcium carbonate, magnesium carbonate, sodium bicarbonate, potassium bicarbonate, calcium bicarbonate, magnesium bicarbonate, tetramethylammonium hydroxide, cetyltrimethylammonium hydroxide, and mixtures thereof.

23. The method of claim 22 wherein the base is selected from the group consisting of sodium hydroxide, potassium hydroxide and lithium hydroxide.

24. The method of claim 18 wherein the amount of base is between about 1.05 and about 1.5 times the stoichiometric amount of base required to destroy the contaminating fluoroalkane.

25. The method of claim 18 wherein each halogen atom in addition to fluorine in the perhalofluorocarbon molecular formula is selected independently from chlorine and bromine.

26. The method of claim 18 in which the refrigerant composition consists essentially of (i) between about 20 percent-by-weight and about 99.5 percent-by-by weight of at least one saturated $C_1$–$C_4$ perhalofluorocarbon, the molecular formula of said perhalofluorocarbon containing no hydrogen atoms but containing, in addition to carbon and at least one fluorine atom, at least one additional halogen atom selected independently from the group consisting of fluorine, chlorine and bromine, together with (ii) between about 0.5 percent-by-weight and about 80 percent-by-weight of at least one contaminating saturated $C_1$–$C_2$ fluoroalkane, the molecular formula of said fluoroalkane containing, in addition to carbon and fluorine, at least one hydrogen atom and at least one halogen atom selected from the group consisting of chlorine, bromine and iodine.

27. The method of claim 18 in which said reagent consists essentially of water and base.

28. The method of claim 18 wherein each perhalofluorocarbon is selected from the group consisting of $C_1$–$C_2$ perhalofluorocarbons.

29. The method of claim 18 wherein each contaminating fluoroalkane is selected from the group consisting of $C_1$ fluoroalkanes.

30. The method of claim 18 wherein the perhalofluorocarbon is selected from the group consisting of fluorotrichloromethane, dichlorodifluoromethane, chlorotrifluoromethane, tetrafluoromethane, and mixtures thereof, and the contaminating fluoroalkane is selected from the group consisting of fluorodichloromethane, chlorodifluoromethane, bromochlorofluoromethane, and mixtures thereof.

31. The method of claim 18 carried out under greater than 1 atmosphere pressure.

32. The method of claim 31 wherein the decontaminated perhalofluorocarbon is simultaneously separated and recovered from the reaction mixture as a gas by venting the headspace of the reaction vessel.

33. The method of claim 18 wherein the molar amount of base is at least 4 times the molar amount of fluoroalkane contained in the contaminated refrigerant composition.

34. The method of claim 18 wherein the liquid reaction mixture consists essentially of two immiscible liquid layers.

35. The method of claim 34 wherein the two liquid layers are separated by decantation, and the decontaminated perhalofluorocarbon is recovered from one of the separated layers.

36. The method of claim 18 wherein the decontaminated perhalofluorocarbon contains no by-product in an amount which disqualifies the decontaminated refrigerant composition from use in refrigeration and air-conditioning equipment.

37. The method of claim 18 wherein the fluoroalkane is a fluoromethane.

38. The method of claim 18 wherein the perhalofluorocarbon refrigerant comprises dichlorodifluoromethane and the fluoroalkane comprises chlorodifluoromethane.

39. A method for purifying a contaminated refrigerant composition which consists essentially of between about 20 percent-by-weight and about 99.5 percent-by-weight dichlorodifluoromethane, together with between about 0.5 percent-by-weight and about 80 percent-by-weight contaminating chlorodifluoromethane, which method comprises (a) producing a heterogeneous liquid/liquid reaction mixture by introducing the contaminated refrigerant composition into a pressurizable reaction vessel, along with a reagent consisting essentially of water and between about 12.5 percent-by-weight and about 95 percent-by-weight base in a molar amount which is at least about 4 times the molar amount of the chlorodifluoromethane in the contaminated refrigerant composition;

(b) mixing and reacting the contents of the reaction vessel while controlling the temperature of the reaction mixture between about 0° C. and about 100° C. and the pressure in the reaction vessel to maintain the refrigerant composition in a predominantly liquid state for a period of time required to decontaminate the dichlorodifluoromethane refrigerant; and (c) separating and recovering the decontaminated dichlorodifluoromethane from the reaction mixture;

whereby the recovered decontaminated dichlorodifluoromethane contains less than 0.5 percent-by-weight contaminating chlorodifluoromethane and no by-product in an amount which otherwise disqualifies the decontaminated dichlorodifluoromethane from use in refrigeration and air-conditioning equipment.

40. A method for purifying a contaminated refrigerant composition which includes (i) between about 89 percent-by-weight and about 99.5 percent-by-weight of at least one saturated $C_1$–$C_4$ perhalofluorocarbon, the molecular formula of said perhalofluorocarbon containing no hydrogen atoms but containing, in addition to carbon and at least one fluorine atom, at least one additional halogen atom selected independently from the group consisting of fluorine, chlorine and bromine, together with (ii) between about 0.5 percent-by-weight and about 11 percent-by-weight of at least one contaminating saturated $C_1$–$C_2$ fluoroalkane, the molecular formula of said fluoroalkane containing, in addition to carbon and fluorine, at least one hydrogen atom and at least one halogen atom selected from the group consisting of chlorine, bromine and iodine, which method comprises (a) producing a heterogeneous liquid/liquid reaction mixture by introducing the contaminated refrigerant composition into a pressurizable reaction vessel, along with a reagent which includes water and base in an amount sufficient to destroy the contaminating fluoroalkane;

(b) mixing and reacting the contents of the reaction vessel while controlling the temperature of the reaction mixture between about 0° C. and about 100° C. and adjusting the pressure in the reaction vessel to maintain the refrigerant composition in a predominantly liquid state for a period of time required to decontaminate the perhalofluorocarbon refrigerant; and (c) separating the aqueous phase from the decontaminated perhalofluorocarbon phase and recovering the decontaminated perhalofluorocarbon refrigerant;

whereby the recovered decontaminated refrigerant contains less than 0.5 percent-by-weight contaminating fluoroalkane.

41. The method of claim 1 wherein said aqueous solution of step (a) contains between about 12.5 percent-by-weight and about 28 percent-by-weight base.

42. The method of claim 41 wherein said aqueous solution of step (a) contains between about 12.5 percent-by-weight and about 25 percent-by-weight base.

43. The method of claim 18 wherein said reagent includes water and between about 12.5 percent-by-weight and about 28 percent-by-weight base.

44. The method of claim 39 wherein said reagent consists essentially of water and between about 12.5 percent-by-weight and about 28 percent-by-weight base.

45. The method of claim 40 wherein said reagent includes water and between about 3 percent-by-weight and about 95 percent-by-weight base.

* * * * *